US010259126B1

(12) United States Patent
Kapczynski et al.

(10) Patent No.: US 10,259,126 B1
(45) Date of Patent: Apr. 16, 2019

(54) MODULAR CABLE STRAIN RELIEF DEVICE FOR ARTICULATED ARM ROBOTIC SYSTEMS

(71) Applicant: Verily Life Sciences LLC, Mountain View, CA (US)

(72) Inventors: Maximilian Kapczynski, Palo Alto, CA (US); Eden Rephaeli, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/729,289

(22) Filed: Oct. 10, 2017

(51) Int. Cl.
*F16M 11/00* (2006.01)
*B25J 19/00* (2006.01)
*F16L 3/10* (2006.01)
*A61B 34/30* (2016.01)
*F16L 3/18* (2006.01)
*A61B 34/00* (2016.01)

(52) U.S. Cl.
CPC .......... *B25J 19/0025* (2013.01); *A61B 34/30* (2016.02); *F16L 3/10* (2013.01); *F16L 3/18* (2013.01); *A61B 2034/305* (2016.02); *A61B 2034/715* (2016.02)

(58) Field of Classification Search
CPC ................................ H02G 1/04; H01R 43/00
See application file for complete search history.

(56) References Cited

U.S. PATENT DOCUMENTS

| 1,828,801 | A | | 10/1931 | Finlayson | |
|---|---|---|---|---|---|
| 3,545,724 | A | * | 12/1970 | Wright | H02G 1/04 254/134.3 PA |
| 4,323,725 | A | | 4/1982 | Muller | |
| 4,373,372 | A | * | 2/1983 | Holt | H01R 43/00 72/406 |
| 6,123,571 | A | | 9/2000 | Craft, Jr. | |
| 7,727,003 | B2 | | 6/2010 | Ceroll et al. | |
| 10,030,790 | B2 | * | 7/2018 | Nakovski | B63B 21/66 |

OTHER PUBLICATIONS

Instructions for Installation of Roboway, Retrieved from internet: http://www.cpsystem.co.kr/html/sub02_01.html?category=6 on Apr. 12, 2017, CPS System Co. Ltd, 4 pages.

* cited by examiner

*Primary Examiner* — Amy J. Sterling
(74) *Attorney, Agent, or Firm* — Christensen O'Connor Johnson Kindness PLLC

(57) ABSTRACT

A device for relief of strain on a cable includes a modular base for mounting, a first arm, a second arm, and a spring assembly. The first arm is pivotally coupled to the modular base. A first proximal end of the first arm is connected to the modular base at a first pivot point for pivoting of the first arm about a first rotational axis. The second arm is coupled to the modular base. A second proximal end of the second arm is connected to the modular base. The spring assembly is coupled to the first arm to provide a clamping force between the first arm and the second arm.

20 Claims, 7 Drawing Sheets

US 10,259,126 B1

MODULAR CABLE STRAIN RELIEF DEVICE FOR ARTICULATED ARM ROBOTIC SYSTEMS

TECHNICAL FIELD

This disclosure relates generally to the field of strain relief devices, and in particular but not exclusively, relates to strain relief devices for robotic systems.

BACKGROUND INFORMATION

Industrial and medical robotic systems are becoming increasingly large, complex, and dexterous. For example, robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, robotically controlled instruments may replace traditional tools to perform surgical motions. Feedback controlled motions may allow for smoother surgical steps than those performed by humans. For example, using a surgical robot for a step such as rib spreading, may result in less damage to the patient's tissue than if the step were performed by a surgeon's hand. Additionally, surgical robots can reduce the amount of time in the operating room by requiring fewer steps to complete a procedure.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
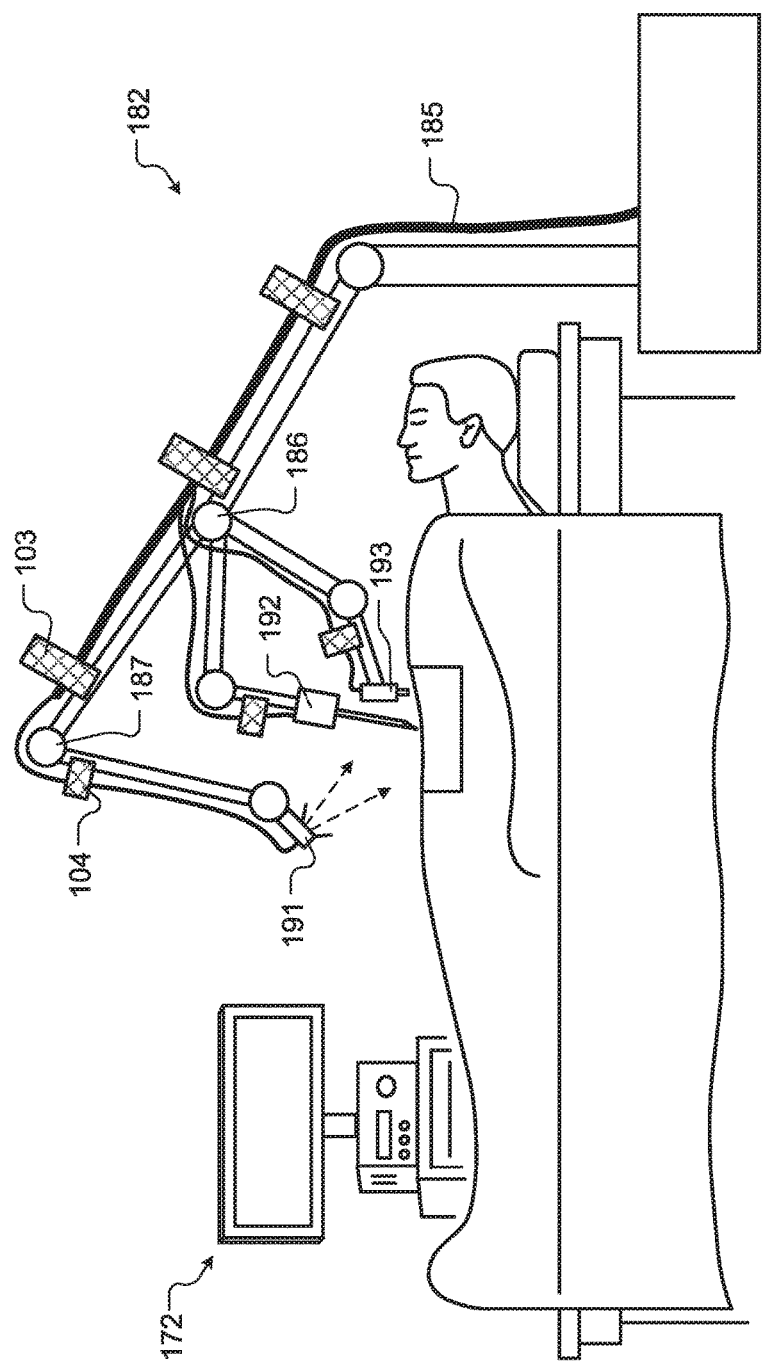
FIG. 1 illustrates a system for robotic surgery, in accordance with an embodiment of the disclosure.

Embodiments of a modular device for cable strain relief are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As the breadth of applications for industrial and medical robotic systems grows, the diversity of robotic end effectors and other devices for these systems follows suit. For example, a modular, multi-use robotic system may support interchangeably hot-swapping end effectors. It may be desirable to hot swap end effectors of a surgical robotic system during steps in a surgical procedure. However, the technical complexity of these end effectors is also ever-increasing and may incorporate specialized supply lines that are distributed to the end effector. These specialized supply lines may include electrical supply lines, pneumatic or hydraulic lines, optical fiber lines for data relay, communication, or high-power illumination, and others.

The desired modularity, compatibility, interoperability, interchangeability, and specialized supply lines of industrial and medical robotic systems pose a significant design challenge. For example, it is desirable for the robotic system to support a variety of end effectors, but such interchangeability may result in increased complexity and cost of the robotic system.

In some embodiments, a complex articulated robotic system may incorporate a number of end effectors, which may introduce a large quantity of supply cabling for supply lines coupled to the end effectors. These supply lines may be delicate, stiff, heavy, temperature sensitive, and/or shock sensitive. Operation of the articulated robotic system may involve one or more large, heavy, and powerful arms that may move in many different directions at a high rate of speed or magnitude of force. This may pose an operating hazard to the cabling for the end effectors. For example, unwanted tangling, twisting, kinking, or shearing of the cabling of the robotic system may inadvertently result in the loss of end effector function and subsequent loss of system functionality.

In the same or other embodiments, a strain relief device may offer an economical and reliable way of protecting end effector cabling of a robotic system. The strain relief device may apply a clamping force to secure the cable in the necessary directions to prevent damage, but may also selectively allow a freedom of motion in other directions in situations where the cable would be damaged if held in place. For example, the strain relief device may allow for the cable to move along a direction during articulation of a robotic arm in a robotic system. The strain relief device may be self-contained and not integral to the robotic system. In other words, an operator may be capable of easily and safely re-positioning the cable within the strain relief device during operation, or reposition the strain relief device itself in order to accommodate a changing operational environment for the robotic system.

FIG. 1 illustrates system 101 for robotic surgery, in accordance with an embodiment of the disclosure. System 101 includes processing apparatus 172 and surgical robot 182. Surgical robot 182 may include joints 186 and 187, a plurality of end effectors (including light source 191, surgical instrument 192, and camera 193), cable 185, and strain relief devices 103 and 104. Processing apparatus 172 may include a display, a processor, memory, local storage, and the like to facilitate the operation of surgical robot 182. As shown, the plurality of end effectors (191, 192, 193) of surgical robot 121 may be used to hold various surgical tools for a surgical procedure (e.g., each arm of the surgical robot holds a surgical tool at the distal ends of the arm) and perform surgery, diagnose disease, take biopsies, or conduct any other procedure a doctor could perform. The surgical tools may include one or more of surgical instrument 192 (e.g., scalpels, forceps, clamps, staplers, probes, etc.), camera 101 (e.g., image sensor), light source 191 (e.g., light-emitting diode, laser, fiber optic, etc.) or the like. The arms of surgical robot 182 may be articulated to allow for precise control of movement and position of surgical robot 182. As illustrated, surgical robot 182 includes joints 186 and 187 to provide the desired articulation of the arms of surgical robot 182. While surgical robot 182 is illustrated as having only three arms and six joints, one skilled in the art will appreciate that surgical robot 182 is merely an illustration, and that surgical robot 182 may take any number of shapes depending on the type of surgery needed to be performed and other requirements.

As illustrated, the plurality of end effectors (191, 192, and 193) of surgical robot 182 is variously coupled to cable 185. Cable 185 provides specialized supply lines such as electrical supply lines, pneumatic or hydraulic lines, optical fiber lines for data relay, communication, or high-power illumination, and others to the plurality of end effectors (191, 192, and 193). Cable 185 may be delicate, stiff, heavy, temperature sensitive, and/or shock sensitive, or otherwise desired to be protected to facilitate operation of surgical system 100. Strain relief devices 103 and 104 are removably mounted to surgical robot 182 and coupled to cable 185 along various points of surgical system 100. Strain relief devices 103 and 104 relieve strain on cable 185, for example, by holding cable 185 in place with varying amounts of resistance to mitigate unwanted tangling, twisting, kinking, or shearing of cable 185. In some embodiments, cable 185 may be held in place by strain relief devices 103 and 104 during articulation of surgical robot 182 to prevent cable 185 from interfering with the movement of surgical robot 182 or others. Alternatively or in addition, strain relief devices 103 and 104 may facilitate the movement of cable 185 along a direction that would otherwise cause cable 185 to be damaged. For example, strain relief devices 103 and 104 allow for cable 185 to be moved along a single direction during articulation of surgical robot 182. This may prevent damage to cable 185 if, for example, there is not enough slack in cable 185 to allow surgical robot 182 to articulate a desired amount.

In some embodiments, cable 185 is a bundle of individual cables necessary for the plurality of end effectors (191, 192, 193). The bundle of individual cables have a thickness greater than any individual cable in the bundle. Thus, in some embodiments, cable 185 may have a single unified size or shape, while in other embodiments, cable 185 may have various sizes and shapes dependent on the configuration of surgical robot 182. Therefore, it is appreciated that a size and shape of strain relief devices 103 and 104 may correspond to a particular size and shape of an individual cable or bundle of cables.

Surgical robot 182 is coupled to processing apparatus 172, which may be coupled to a network and/or external storage either by wires or wirelessly. Furthermore, surgical robot 182 may be coupled (wirelessly or by wires) to a user input/controller to receive instructions from a surgeon or doctor. The controller, and user of the controller, may be located very close to surgical robot 182 and patient (e.g., in the same room) or may be located many miles apart. Thus surgical robot 182 may be used to perform surgery where a specialist is many miles away from the patient, and instructions from the surgeon are sent over the internet or secure network. Alternatively, the surgeon may be local and may simply prefer using surgical robot 182 because it can better access a portion of the body than the hand of the surgeon could.

Figure 2A:
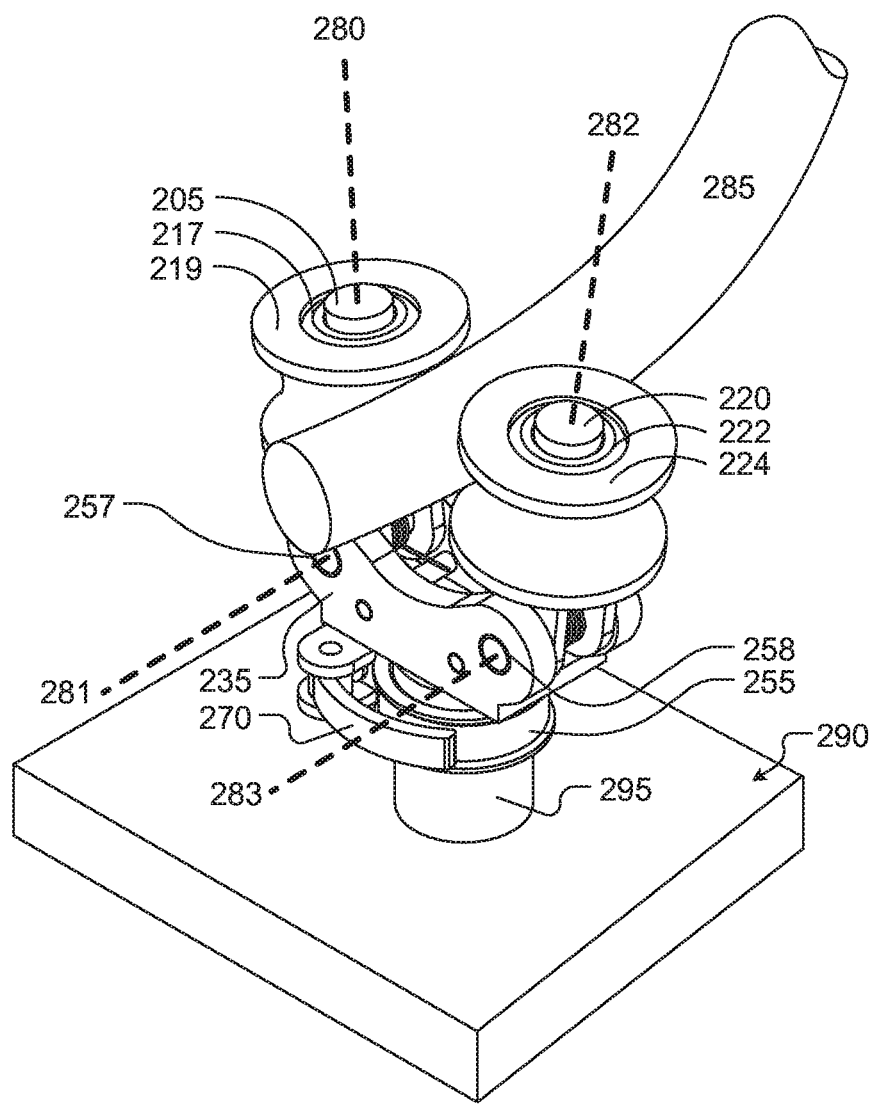
FIG. 2A illustrates a perspective view of a strain relief device, in accordance with an embodiment of the disclosure.
Figure 2B:
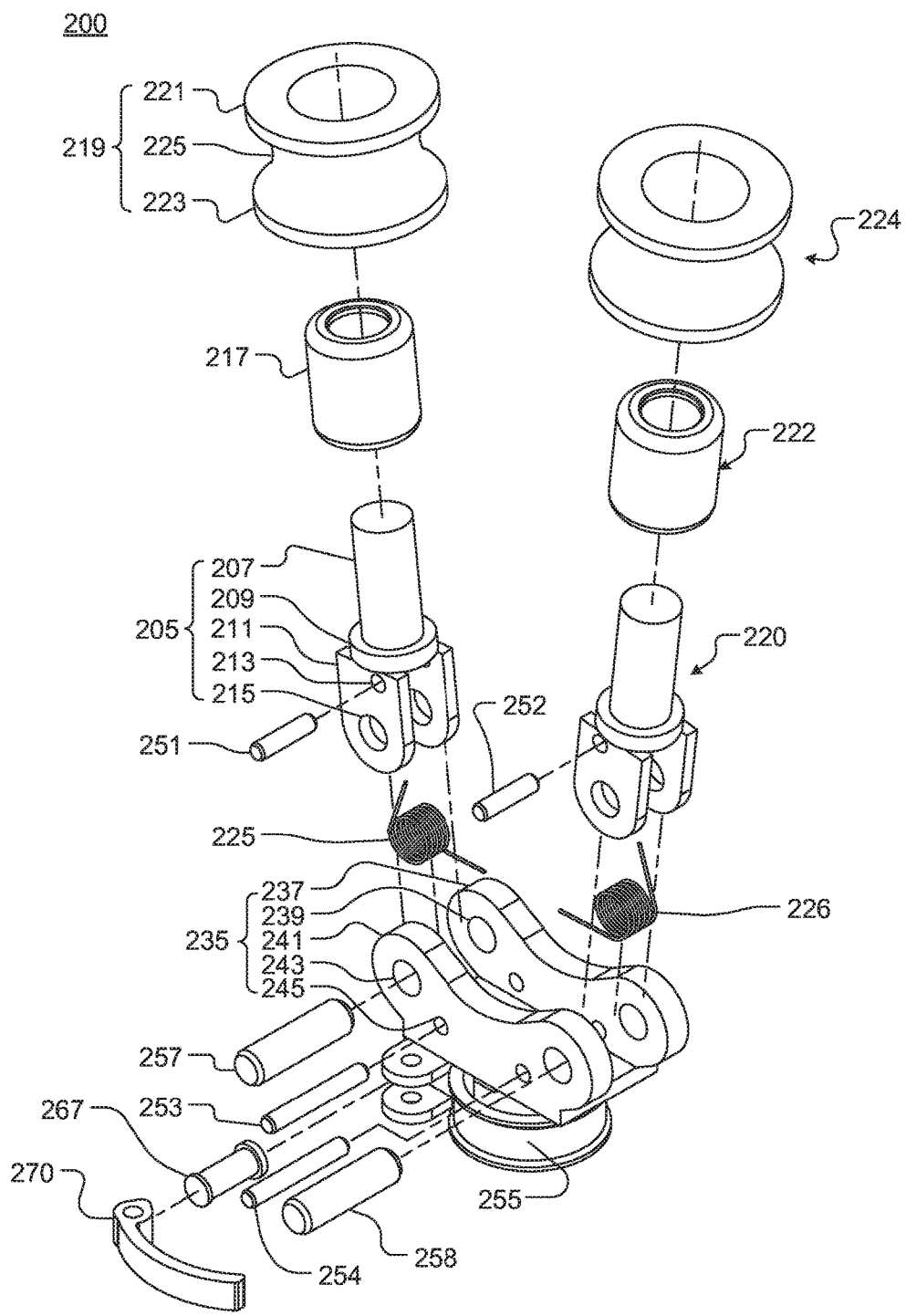
FIG. 2B illustrates an exploded view of a strain relief device, in accordance with an embodiment of the disclosure.
Figure 2C:
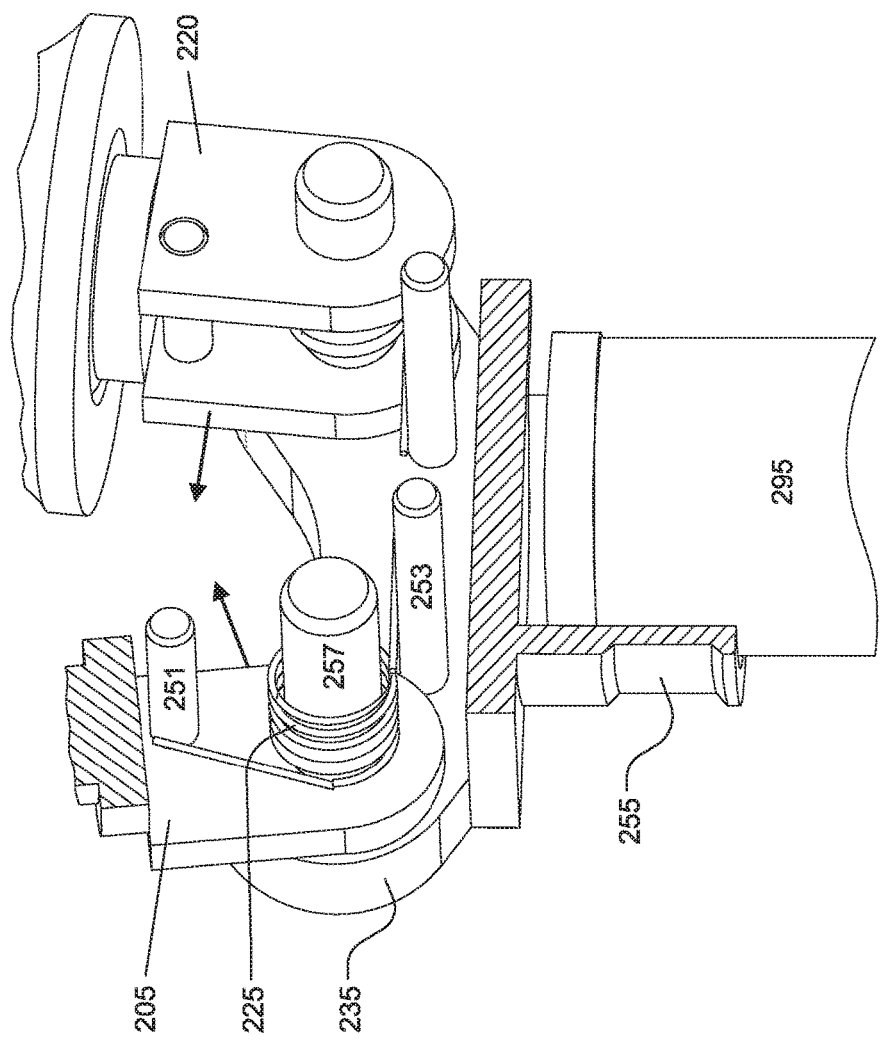
FIG. 2C illustrates a cross-sectional view of a strain relief device, in accordance with an embodiment of the disclosure.

FIGS. 2A-2C illustrate three views of strain relief device 200, in accordance with various embodiments of the disclosure. Strain relief device 200 is one possible implementation of strain relief devices 103 and 104 illustrated in FIG. 1. The illustrated embodiment of strain relief device 200 includes modular base 235 (including first base plate 237 and second base plate 241), first arm 205, second arm 220, first locking clutch 217, second locking clutch 222, first roller 219, second roller 224, spring assembly (including first torsion spring 225 and second torsion spring 226), first stop pin 251, second stop pin 253, third stop pin 252, fourth stop pin 254, first pivot pin 257, second pivot pin 258, mounting feature 255, latch pin 267, and latch handle 270.

FIG. 2A illustrates a perspective view of strain relief device 200, in accordance with an embodiment of the disclosure. Strain relief device 200 is mounted to feature 295 of object 290. Object 290 may be a wall, table, industrial robotic system, medical robotic system, and the like. Feature 295 is a designed location for mounting strain relief device 200. In some embodiments, feature 295 may be a rigid post. In other embodiments, feature 295 may be a pivotable or flexible feature. For example, feature 295 may be a free pivot, a ball-socket, or a flexible member to free up or constrain degrees of freedom as required by a particular application. In one embodiment, strain relief device 200 is mounted to an articulated robotic arm of the medical robotic system and is configured to apply a clamping force to cable 285 to relieve strain on cable 285.

As illustrated, modular base 235 is for mounting strain relief device 200 (e.g., to feature 295 of object 290). Strain relief device 200 includes first arm 205 pivotally coupled to modular base 235. In particular, a first proximal end of first arm 205 is connected to modular base 235 at a first pivot point (e.g., with first pivot pin 257) for pivoting of first arm 205 about a first rotational axis 281. Similarly, second arm 220 is pivotally coupled to modular base 235. A second proximal end of second arm 220 is connected to modular base 235 at a second pivot point (e.g., with second pivot pin 258) for pivoting of second arm 220 about a second rotational axis 283. Pivoting of the arms (e.g., first arm 205 and second arm 220) allows for a position of the arms to change to allow for cable 285 to be inserted and/or removed from between first arm 205 and second arm 220. The spring assembly (e.g., first torsion spring 225) is coupled to first arm 205 to provide a clamping force between first arm 205 and second arm 220. The clamping force may be able to be applied, at least in part, because first arm 205 and/or second arm 220 is able to pivot about first rotational axis 281 and second rotational axis 283, respectively, rather than being fixed in position.

In some embodiments, first rotational axis 281 is parallel to second rotational axis 283 such that the first arm 205 is aligned with second arm 220 (e.g., the center of first arm 205 is aligned with the center of second arm 220 along a line perpendicular to first rotational axis 281 and second rotational axis 283). In the same or other embodiments, one of first arm 205 or second arm 220 may be fixed in position to modular base 235 while the other arm is pivotally coupled. For example, first arm 205 may be pivotally coupled to modular base 235, while second arm 220 may be statically coupled to modular base 235 (e.g., a second proximal end of the second arm is connected to the modular base at a fixed position). In such an embodiment, modular strain device 200 may have a reduced complexity, but still allow for one of the first arm 205 or second arm 220 to change in position so cable 285 may be inserted and/or removed from between first arm 205 and second arm 220.

As illustrated, a first roller 219 is coupled to first arm 205 proximate to a first distal end of first arm 205. First roller 219 is positioned to rotate about third rotational axis 280, which in the illustrated embodiment extends longitudinally through first arm 205. Similarly, a second roller 224 is coupled to second arm 220 proximate to a second distal end of second arm 220. Second roller 224 is positioned to rotate about fourth rotational axis 282 which in the illustrated embodiment extends longitudinally through second arm 220. First roller 219 and second roller 224 may be free rollers which allows for bidirectional rotation or may be locking rollers which only allow for unidirectional rotation. In other words, depending on the configuration of strain relief device 200, first roller 219 and second roller 224 may each allow for only clockwise rotation, only counter clockwise rotation, or both clockwise and counterclockwise rotation.

In the illustrated embodiment, first locking clutch 217 (e.g., a one way sprag clutch) is disposed between first roller 219 and first arm 205 to configure first roller 219 to only allow for unidirectional rotation along third rotational axis 280. Similarly, second locking clutch 222 is disposed between second roller 224 and second arm 220 to configure second roller 224 to only allow for unidirectional rotation about fourth rotational axis 282. In other embodiments, a ball bearing is disposed between first roller 219 and first arm 205 and/or second roller 224 and arm 220 to allow for bidirectional rotation of first roller 219 and/or second roller 224. In some embodiments, third rotational axis 280 is orthogonal to first rotational axis 281 and fourth rotational axis 282 is orthogonal to second rotational axis 283, which may help facilitate first arm 205 and first roller 219 aligning with second arm 220 and second roller 224.

FIG. 2B illustrates an exploded view of strain relief device 200, in accordance with an embodiment of the disclosure. The exploded view may allow for a clear visualization of the various elements of strain relief device 200.

As illustrated, first roller 219 and second roller 224 share a common shape. The shape of first roller 219 and second roller 224 is an annular cylindroid having a radius that decreases longitudinally towards a midpoint of the annular cylindroid. For example, the radius of first end 221 of first roller 219 may be the same as the radius of the second end 223. The radius of first end 221 and second end 223 gradually decreases towards the midpoint 225 of first roller 219. Such a change in radius of first roller 219 creates a contoured external surface of first roller 219 that is an inverse shape of a surface of cable 285. In other words, the external surface of first roller 219 or second roller 224 is shaped in a way that increases the contact area of first roller 205 and second roller 220 with a cable (e.g., cable 285 illustrated in FIG. 2A). The increased contact area of first roller 219 and second roller 224 to the cable may increase the frictional resistance of the cable to move. Thus, the ease of adjusting the position of the cable while clamped may be determined, in part, by the contact area/frictional resistance.

In the illustrated example, first arm 205 includes first distal end 207, a cylindrical stopper 209, and a first proximal end 211. First distal end 207 is opposite of first proximal end 211. First distal end 207 is cylindrical having a radius that is less than cylindrical stopper 209. Cylindrical stopper 209 may help facilitate maintaining locking clutch 217 and first roller 219 at a fixed position on first arm 205. First proximal end 213 includes first stopper pin hole 213 and first pivot pin hole 215 to allow for pivoting of first arm 205, in accordance with an embodiment of the disclosure. Proximal end 215 includes a first arm plate and a second arm plate separated by a distance to allow for torsion spring 225 to be placed between the first arm plate and the second arm plate.

As illustrated, modular base 235 includes first base plate 237 parallel to second base plate 241. First proximal end 211 of first arm 205 and second proximal end of second arm 220 are disposed between first base plate 237 and second base plate 241. Each of the base plates (237 and 241) having corresponding holes for first pivot pin 257, second pivot pin 258, second stop pin 253, and fourth stop pin 254 to facilitate the pivoting of the corresponding arm (205 and 220) and the clamping force. For example, second base plate 241 has first pivot pin hole 243 for first pivot pin 256 and second stop pin hole 245 for second stop pin 253. In some embodiments, first base plate 237 and second base plate 241 each have a saddle shape that has an indentation or gradually decreasing height towards the midpoint. This saddle shape may allow for base 235 to fully enclose some components of strain relief device 200 (e.g., the spring assembly) without touching the cable (e.g. cable 285 illustrated in FIG. 2A).

Referring back to FIG. 2B, modular base 235 is configured to removably mount to an object via latch handle 270, latch pin 267, and mounting feature 255. Latch handle 270 adjusts a magnitude of a force applied to an object such that a compressive and/or frictional force holds strain relief device 200 to the object. For example, latch handle 270 may control the magnitude of the force applied by mounting feature 255 of modular base 235 to the object (e.g., feature 295 of object 290 illustrated in FIG. 2A). Thus latch handle 270 and latch pin 267 of modular base 235 acts as a quick release mechanism to quickly mount and/or unmount strain relief device 200 from object 290.

FIG. 2C illustrates a cross-sectional view of strain relief device 200, in accordance with an embodiment of the disclosure. The cross-sectional view allows for a clear view of a portion of the spring assembly of strain relief device 200.

As illustrated, the spring assembly of strain relief device 200 includes first torsion spring 225 coupled to modular base 235 and the first proximal end of first arm 205. First torsion spring 225 is coiled around first pivot pin 257 and has a first end coupled to first stop pin 251 and a second end coupled to second stop pin 253. First stop pin is coupled to first arm 205 and second stop pin is coupled to modular base 235 meaning first torsion pin 225 applies a first force (e.g., a first torque included in the clamping force) between first arm 205 and modular base 235. As illustrated, the first force is directed from first arm 205 to second arm 220. Second arm 220 may be similarly configured as first arm 205. For example, second torsion spring 226 is coupled to modular base 235 and the second proximal end of second arm 220. Second torsion spring 226 is coiled around second pivot pin 258 and has ends coupled to third stop pin 252 and fourth stop pin 254. Thus, second torsion spring 226 provides a second force (e.g., a second torque included in the clamping force) between second arm 220 and modular base 235. The second force is directed from second arm 220 toward first arm 205 such that the combined first force and second force generates a compressive force on the cable (e.g., cable 285) inserted between first arm 205 and second arm 220.

As illustrated, first torsion spring 225 and second torsion spring 226 are fully contained within modular base 235, which may protect the spring assembly from damage. This may be achieved, in part, because the first proximal end of first arm 205 is positioned between first torsion spring 225 and modular base 235. Similarly, the second proximal end of second arm 220 is positioned between second torsion spring 226 and modular base 235. Due to this arrangement, the spring assembly is fully contained within modular base 235 and does not come in direct contact with the cable (e.g. cable 285).

FIGS. 3A-3D illustrate a method of operation of strain relief device 300, in accordance with an embodiment of the disclosure. Strain relief device 300 provides relief of strain on a cable and may be the same or a similar implementation of strain relief device 200 illustrated in FIGS. 2A-2C. Referring back to FIGS. 3A-3D, strain relief device 300 includes first arm 305, second arm 320, first roller 317, second roller 324, first locking clutch 317, ball bearing 322, first torsion spring 325, second torsion spring 326, modular base 335, latch handle 370, and mounting feature 355.

Figure 3A:
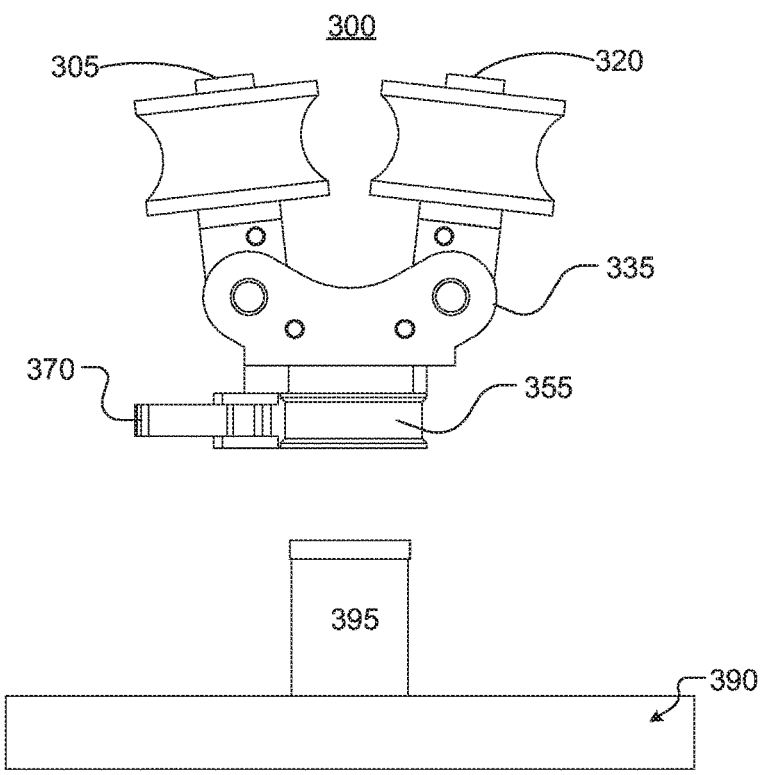
FIGS. 3A-3D illustrate a method of operation of a strain relief device, in accordance with an embodiment of the disclosure.
Figure 3B:
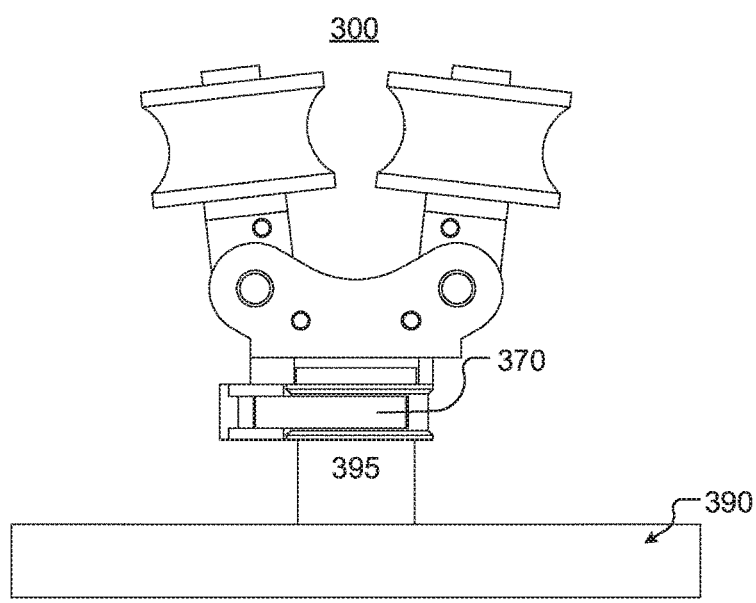

FIG. 3A illustrates opening latch handle 370 such that mounting feature 355 increases in radius to allow for placement of strain relief device 300 on feature 395 of object 390. Mounting feature 355 is subsequently aligned with and then placed on feature 395 of object 390. Latch handle 370 is then closed to hold strain relief device 300 in placed and attached to object 390, as illustrated in FIG. 3B. Once closed, latch handle 370 causes the radius of mounting feature 355 to decrease which in turn generates a compressive force on feature 395 that mounts strain relief device 300 to object 390.

Figure 3C:
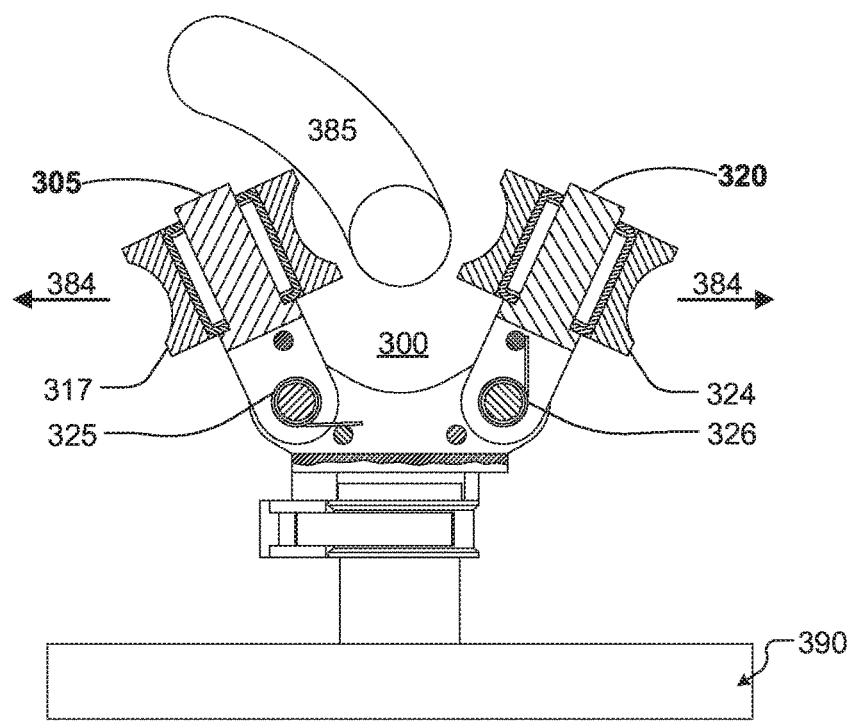

FIG. 3C illustrates placing cable 385 between first arm 305 and second arm 320. This is accomplished by separating first arm 305 and second arm 320 with an external force 384 (e.g., manual manipulation of first arm 305 and second arm 320 via an operator of strain relief device 300) that causes first arm 305 and second arm 320 to pivot about the respective midpoints of first torsion spring 325 and second torsion spring 326.

Figure 3D:
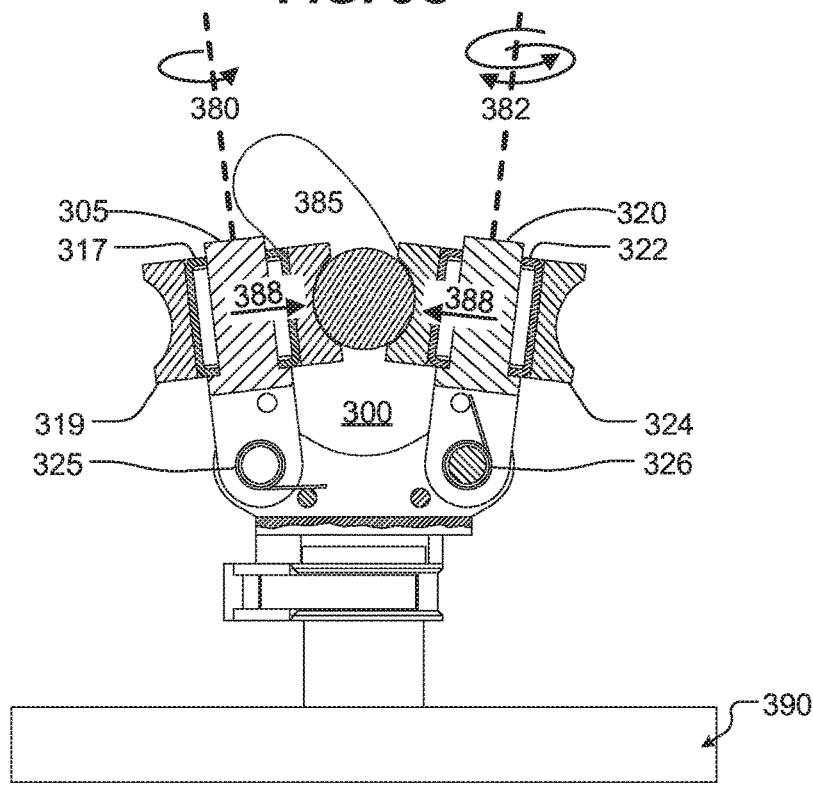

As illustrated in FIG. 3D, once external force 384 is released, first roller 319 of first arm 305 second roller 324 of second arm 320 clamp onto cable 385 and hold cable 385 in place with compressive force 388. While clamped, cable 385 is able to move along a single direction (e.g. out of the plane of the page) due to the allowable rotational directions of first roller 319 and second roller 324. First roller 319 is only able to rotate unidirectionally (e.g., counter clockwise) about rotational axis 380, due in part, because first locking clutch 317 is disposed between first arm 305 and first roller 319, which restricts first roller 319 to a single rotational direction. Second roller 324 is able to rotate bidirectionally (e.g., clockwise and counter clockwise) about rotational axis 382, due in part, because ball bearing 319 is disposed between second roller 324 and second arm 320.

Figure 4:
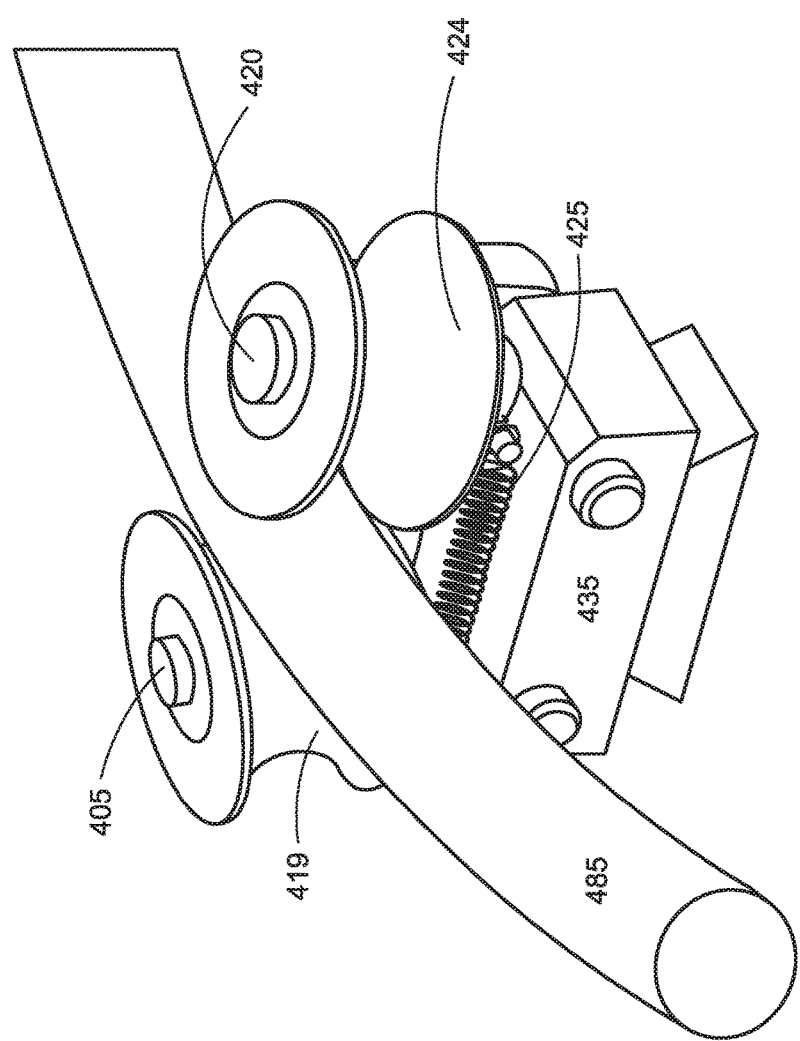
FIG. 4 illustrates a perspective view of a strain relief device, in accordance with an embodiment of the disclosure.

FIG. 4 illustrates a perspective view of strain relief device 400, in accordance with an embodiment of the disclosure. Strain relief device 400 is one possible implementation of strain relief devices 103 and 104 illustrated in FIG. 1. The illustrated embodiment of strain relief device 400 is similar to, but comparably less complex than strain relief device 200 illustrated in FIGS. 2A-2C.

As illustrated, strain relief device 400 includes first arm 405, second arm 420, tension spring 425, and modular base 435. Strain relief device 400 is configured to be removably mounted to an object via a mounting feature (e.g., an articulated arm of a robotic system). In the illustrated case, the mounting feature of strain relief device 400 is a dovetail, but may have any other structure that facilitates mounting of strain relief device 400 to the object. First arm 405 and second arm 420 are pivotally coupled to modular base 420 and thus are able to pivot about their respective rotational axes. Tension spring 425 is coupled to first arm 405 and second arm 420 and generates a clamping force that holds cable 485 in place when positioned between first arm 405 and second arm 420.

In reference to embodiments of the disclosure, a roller, an arm, a locking clutch, and/or a ball bearing are described for restricting the rotation of the roller and movement of the clamped cable. However, it is appreciated that other configurations may also allow for the restriction of the rotation of the roller and/or movement of the clamped cable. For example, instead of a roller coupled to an arm turning within a statically located locking clutch, the roller and locking clutch could be a single unit turning on a statically located arm. Additionally, or alternatively, a paired linear sequence of smaller rollers that rotate unidirectionally could be utilized in place of the two rollers.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A device for relief of strain on a cable, comprising:
    a modular base for mounting the device;
    a first arm pivotally coupled to the modular base, wherein a first proximal end of the first arm is connected to the modular base at a first pivot point for pivoting of the first arm about a first rotational axis;
    a second arm coupled to the modular base, wherein a second proximal end of the second arm is connected to the modular base;
    a spring assembly coupled to the first arm to provide a clamping force between the first arm and the second arm;
    a first roller coupled to the first arm and configured to rotate unidirectionally about a third rotational axis; and
    a second roller coupled to the second arm and configured to rotate bidirectionally about a fourth rotational axis.

2. The device of claim 1, wherein the second arm is pivotally coupled to the modular base, and wherein the second proximal end of the second arm is connected to the modular base at a second pivot point for pivoting of the second arm about a second rotational axis.

3. The device of claim 1, wherein the first roller is configured to rotate unidirectionally about the third rotational axis via a first locking clutch disposed between the first roller and the first arm.

4. A device for relief of strain on a cable, comprising:
a modular base for mounting the device;
a first arm pivotally coupled to the modular base, wherein a first proximal end of the first arm is connected to the modular base at a first pivot point for pivoting of the first arm about a first rotational axis;
a second arm pivotally coupled to the modular base, wherein a second proximal end of the second arm is connected to the modular base at a second pivot point for pivoting of the second arm about a second rotational axis;
a first roller coupled to the first arm and configured to rotate unidirectionally about a third rotational axis via a first locking clutch disposed between the first arm and the first roller; and
a second roller coupled to the second arm and configured to rotate unidirectionally about a fourth rotational axis via a second locking clutch disposed between the second arm and the second roller.

5. The device of claim 1, wherein the first roller is disposed proximate to a first distal end of the first arm, wherein the first distal end is opposite of the first proximal end, wherein the second roller is disposed proximate to a second distal end of the second arm, wherein the second distal end is opposite of the second proximal end.

6. The device of claim 2, wherein the first rotational axis is different than the second rotational axis, and wherein the first rotational axis is parallel to the second rotational axis.

7. The device of claim 2, wherein the spring assembly includes:
a first torsion spring coupled to the modular base and the first proximal end of the first arm, wherein the first torsion spring is configured to provide a first force, included in the clamping force, directed from the first arm toward the second arm; and
a second torsion spring coupled to the modular base and the second proximal end of the second arm, wherein the second torsion spring is configured to provide a second force, included in the clamping force, directed from the second arm toward the first arm.

8. The device of claim 6, wherein the first proximal end of the first arm is positioned between the first torsion spring and the modular base, wherein the second proximal end of the second arm is positioned between the second torsion spring and the modular base.

9. The device of claim 2, wherein a shape of the first roller and the second roller is an annular cylindroid having a radius that decreases longitudinally towards a midpoint of the annular cylindroid.

10. The device of claim 2, wherein the first rotational axis is orthogonal to the third rotational axis, and wherein the second rotational axis is orthogonal to the fourth rotational axis.

11. The device of claim 1, wherein the spring assembly includes a tension spring coupled to the first arm and the second arm to provide the clamping force.

12. The device of claim 1, wherein the modular base includes a first base plate parallel to a second base plate, wherein the first proximal end of the first arm and the second proximal end of the second arm are disposed between the first base plate and the second base plate.

13. The device of claim 1, wherein the modular base is configured to removably mount to an object via a latch handle and a latch pin, each coupled to the modular base, wherein the latch handle adjusts a magnitude of a compressive force applied by the modular base to the object.

14. A robotic surgical system, the system comprising:
an articulated robotic arm including at least one joint to provide articulation of the robotic arm;
an end effector coupled to a distal end of the articulated robotic arm;
a cable extending along the articulated robotic arm, wherein the cable is coupled to the end effector; and
a strain relief device coupled to the cable and the articulated robotic arm to provide relief of strain on the cable, wherein the strain relief device includes:
a modular base configured to be removably mounted to the articulated robotic arm;
a first arm pivotally coupled to the modular base, wherein a first proximal end of the first arm is connected to the modular base at a first pivot point for pivoting of the first arm about a first rotational axis;
a second arm coupled to the modular base, wherein a second proximal end of the second arm is connected to the modular base;
a spring assembly coupled to the first arm to provide a clamping force on the cable positioned between the first arm and the second arm, wherein the clamping force is a compressive force applied to the cable by the first arm and the second arm.

15. The system of claim 14, wherein the second arm of the strain relief device is pivotally coupled to the modular base, and wherein the second proximal end of the second arm is connected to the modular base at a second pivot point for pivoting of the second arm about a second rotational axis.

16. The system of claim 14, wherein the strain relief device further includes:
a first roller coupled to the first arm proximate to a first distal end of the first arm, wherein the first distal end is opposite of the first proximal end, and wherein the first roller is coupled to rotate about a third rotational axis; and
a second roller coupled to the second arm proximate to a second distal end of the second arm, where the second distal end is opposite of the second proximal end, and wherein the second roller is coupled to rotate about a fourth rotational axis.

17. The system of claim 16, wherein the strain relief device further includes:
a first locking clutch disposed between the first roller and the first arm, wherein the first roller is configured to rotate unidirectionally about the third rotational axis due to the first locking clutch.

18. The system of claim 17, wherein the strain relief device further includes:
a second locking clutch disposed between the second roller and the second arm, wherein the second roller is configured to rotate unidirectionally about the fourth rotational axis due to the second locking clutch.

19. The system of claim 18, wherein the second roller of the strain relief device is a free roller configured to rotate bidirectionally about the fourth rotational axis.

20. A device for relief of strain on a cable, comprising:
a modular base for mounting the device;
a first arm coupled to the modular base, wherein a first proximal end of the first arm is connected to the modular base;
a second arm coupled to the modular base, wherein a second proximal end of the second arm is connected to the modular base, wherein at least one of the first arm or the second arm is pivotally coupled to the modular base;

a spring assembly coupled to the first arm or the second arm to provide a clamping force between the first arm and the second arm;

a first roller coupled to the first arm and configured to rotate unidirectionally about a third rotational axis; and a second roller coupled to the second arm and configured to rotate bidirectionally about a fourth rotational axis.

* * * * *